United States Patent
Brunfeld et al.

(10) Patent No.: US 6,255,666 B1
(45) Date of Patent: *Jul. 3, 2001

(54) HIGH SPEED OPTICAL INSPECTION APPARATUS FOR A LARGE TRANSPARENT FLAT PANEL USING GAUSSIAN DISTRIBUTION ANALYSIS AND METHOD THEREFOR

(75) Inventors: Andrei Brunfeld, Bat-Yam; Joseph Shamir, Haifa; Gregory Toker, Jerusalem; Liviu Singher, Haifa; Ilan Laver; Ely Pekel, both of Kefar Saba, all of (IL)

(73) Assignee: Brown & Sharpe Surface Inspection Systems, Inc., North Kingstown, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/985,629

(22) Filed: Dec. 3, 1992

(51) Int. Cl.[7] .................................................. G01H 21/88
(52) U.S. Cl. .................................. 250/559.45; 356/239.1
(58) Field of Search .................................. 250/234–236, 250/562, 563, 559.45, 559.48, 559.49; 356/238, 239, 429–431, 237.2, 239.1; 364/507; 209/588

(56) References Cited

U.S. PATENT DOCUMENTS

| | | | | |
|---|---|---|---|---|
| 3,900,265 | * | 8/1975 | Merlen et al. | 250/572 |
| 4,265,545 | * | 5/1981 | Slaker | 250/572 |
| 4,376,583 | * | 3/1983 | Alford et al. | 356/237 |
| 4,455,086 | * | 6/1984 | West et al. | 356/239 |
| 4,570,074 | * | 2/1986 | Jette | 250/572 |
| 4,725,139 | * | 2/1988 | Hack et al. | 356/239 |
| 5,026,983 | * | 6/1991 | Meyn | 250/563 |
| 5,157,266 | * | 10/1992 | Schmiedl | 250/563 |

* cited by examiner

Primary Examiner—Stephone B. Allen
(74) Attorney, Agent, or Firm—Wolf, Greenfield & Sacks, P.C.

(57) ABSTRACT

An optical inspection apparatus operates at high speed at very high resolution for detecting defects in transparent flat panels in a production environment. This apparatus uses a laser which provides a light beam directed to a polygon scanner, which provides a linear scan of the beam along the width of the flat panel. The flat panel to be inspected is moved such that its entire surface passes the scan path of the light beam. The light beam passes through the transparent flat panel, and is reflected off a spherical mirror, back through the transparent flat panel, and returns to the scanning optics and the polygon scanner in a path coincident with the transmitted light beam. The reflected light beam is distinguished from the transmitted light beam by using a beam splitter to direct the reflected light beam to a parallel detector array, which detects changes in the nominal Gaussian distribution of the light beam that correspond to defects in the surface of the transparent flat panel above a programmable threshold level. This parallel detection method allows the inspection apparatus to identify defects much smaller than the diffraction limits of the optics used, and will accurately identify changes in the light beam caused by defects in the flat panel. An automatic flat panel handler loads untested flat panels into the apparatus and unloads and sorts tested flat panels according to the results of the inspection.

75 Claims, 7 Drawing Sheets

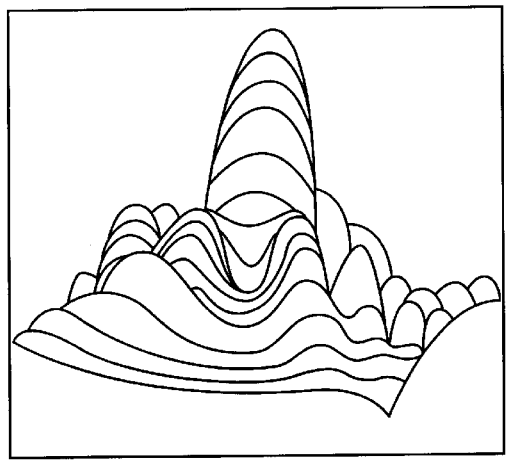
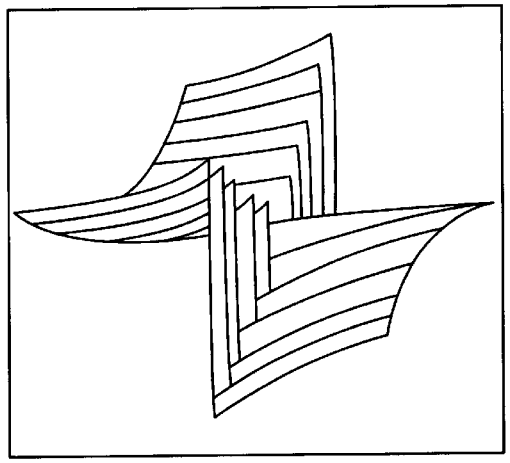
FIG. 7a  FIG. 7b
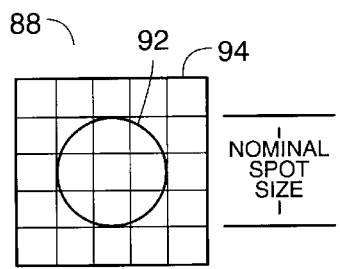
FIG. 8
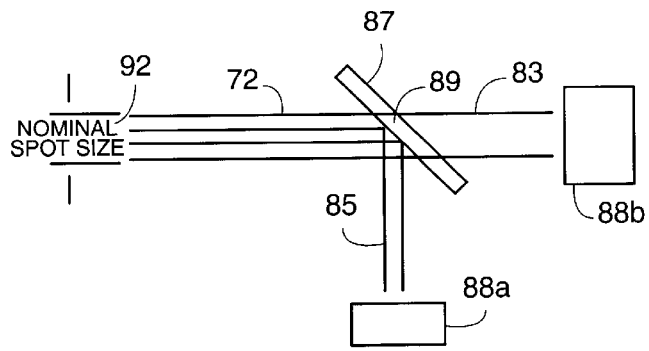
FIG. 8b
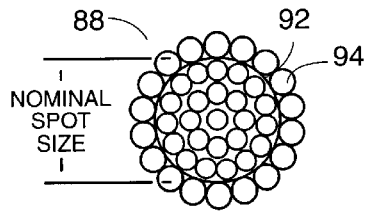
FIG. 8a
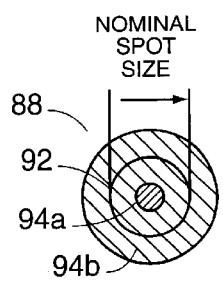
FIG. 8c

HIGH SPEED OPTICAL INSPECTION APPARATUS FOR A LARGE TRANSPARENT FLAT PANEL USING GAUSSIAN DISTRIBUTION ANALYSIS AND METHOD THEREFOR

RELATED APPLICATIONS

This patent application is related to three other U.S. patent applications entitled: "High Speed Optical Inspection Apparatus and Method", "High Speed Optical Inspection Apparatus for a Transparent Disk and Method Therefor", and "High Speed Optical Inspection Apparatus for a Reflective Disk and Method Therefor", which are assigned to the same assignee as this patent application and which are filed on the same date as the date of this patent application.

FIELD OF THE INVENTION

This invention generally relates to optical apparatus and methods, and relates, more specifically, to an optical inspection apparatus and method for detecting faults in a flat, polished flat panel, such as those commonly used in Liquid Crystal Display (LCD) panels. This apparatus inspects with high resolution at high speed with automatic handling of the flat panel to allow the apparatus to be used effectively in a production inspection environment.

DESCRIPTION OF THE PRIOR ART

Flat panels for LCD panels require a surface that is flat to a high degree of accuracy, and that is free from defects such as scratches and chips. Some optical inspection systems have been used with limited success in inspecting transparent flat panels, but do not provide the accuracy or speed that is needed in a production environment.

Dark field microscopes and scatterometers are inspection apparatus well-known in the art. A dark field microscope can somewhat accurately locate surface defects, but takes too long to inspect to be effectively used in a production environment. A scatterometer is faster than a dark field microscope, but has less accuracy (detects fewer defects). Both the dark field microscope and the scatterometer have low detection sensitivity to shallow defects or defects that have a depth less than the wavelength of the light used, which cause a phase shift in the light beam but do not diffuse (scatter) the light in different directions. An interferometer, which is well-known in the art, is suitable to detecting phase shifts, but takes substantial time and effort to set up, limiting its use to laboratory environments.

The inherent limitations of the prior art inspection systems have limited their use in industrial production environments. Indeed, the most common inspection method used in a production environment is a manual, visual inspection by human inspectors, which hold the flat panel in their hands and move the flat panel in ambient or special light looking for the presence of scratches, chips and other defects. This inspection method is labor intensive, relatively slow, and subject to human errors such as missed defects which the human eye cannot easily distinguish.

Therefore, there existed a need to provide a high speed optical inspection system and method which has a high sensitivity to defects which can be used to inspect transparent flat panels in a production environment. This inspection system includes automatic handling of the flat panels, high speed inspection, and high resolution to detect defects smaller that the spot size of the beam and/or more shallow than the wavelength of light used. The increased speed of this apparatus increases throughput of the production system, and assures that any mistakes or defects introduced by human inspectors is eliminated.

SUMMARY OF THE INVENTION

It is an object of this invention to provide a high-speed optical inspection apparatus and method suitable for production testing of transparent flat panels.

It is another object of this invention to provide a high speed optical inspection apparatus and method which is computer-controlled using an IBM PC-AT computer or equivalent.

It is a further object of this invention to provide a high speed optical inspection apparatus and method with surface inspection which has a high speed optical scanner to provide linear movement of the beam across one axis of the flat panel, and a flat panel actuator to move the flat panel, thereby positioning each portion of the flat panel in the path of the linear movement of the beam, thereby completely inspecting the entire face surface of the flat panel.

It is yet another object of this invention to provide a high speed optical inspection apparatus and method which has an Automatic Flat Panel Handler for automatically loading the flat panels into the apparatus and for automatically unloading the flat panels from the apparatus.

It is a still further object of this invention to provide a high speed optical inspection apparatus and method which detects both phase and amplitude changes of the light beam using multiple detectors to sense changes in the nominal Gaussian distribution of the light beam.

It is yet another object of this invention to provide a high speed optical inspection apparatus and method which has a trigger detector within the path of the scanning light beam to provide a signal to synchronize the controlling computer to the scan of the light beam.

According to the preferred embodiment of the present invention, an optical inspection apparatus for inspecting a transparent flat panel is provided. This inspection apparatus is controlled by an IBM PC-AT computer or equivalent, and has a typical color monitor, printer and keyboard. An Optical Inspection Assembly is provided which comprises a Surface Inspection Assembly. The Surface Inspection Assembly nominally comprises a laser light source which transmits a light beam, a high-speed Optical Scanner, Scanning Optics, a beam splitter, optional Detection Optics, and a Parallel Detector Array within a Detector. In this configuration the light beam in the Surface Inspection Assembly originates in the laser, is transmitted through a filter, and is transmitted to the Optical Scanner, which reflects the light beam off the moving polygonal scanner head, causing the light beam to sweep across the Scanning Optics.

The size of a flat panel can be much greater than the size of a practical lens. Placing the Optical Scanner at a distance from the Scanning Optics less than the focal length of the Scanning Optics causes the light beam to diverge at the Scanning Optics, making the beam sweep a distance larger than the diameter of the lens. The beam is focused at the center of the transparent flat panel media by the Scanning optics. On the opposite side of the flat panel is a strip of a spherical mirror which reflects the divergent beam back through the Scanning Optics to the Optical Scanner. This reflected beam is distinguished from the transmitted beam using a beam splitter between the laser and the Optical Scanner. The reflected beam is then directed to the Parallel Detector Array, which detects defects in the flat panel above a programmable threshold. This array is typically a matrix of photodiodes or Charge-Coupled Devices (CCDs) upon which the light beam is projected. This matrix configuration provides a two dimensional Gaussian response with respect to light intensity (amplitude). Any defect in the flat panel deflects light from the Parallel Detector Array (causing a change in the nominal light level) or shifts its phase (causing a change in the Gaussian distribution), both of which are detected by the processing electronics coupled to the Parallel Detector Array. Thus the processing electronics simply look for changes in the nominal level or distribution of the Gaussian response provided by the Parallel Detector Array in response to a nominal light beam, which changes correspond to surface defects an a transparent flat panel.

In this preferred embodiment, the flat panel is placed on an actuator that positions the flat panel such that the scanning begins at the top of the flat panel and moves down. Once the Optical Scanner beam completes one scan, the panel is raised to the next position, and the scanning continues in like manner until the entire surface of the flat panel has been inspected. The computer controls the movement of the flat panel to assure the entire surface is scanned. If the Surface Inspection Assembly detects a defect greater than its programmed threshold, a fault signal is sent to the computer to indicate the flat panel failed the inspection.

The foregoing and other objects, features and advantages will be apparent from the following description of the preferred embodiments of the invention as illustrated in the accompanying drawings.

BRIEF DESCRIPTION OF THE DRAWINGS

FIG. 7a is a three dimensional representation of a typical Gaussian response of light intensity (amplitude).

FIG. 7b is a three dimensional representation of a typical Gaussian response of light phase.

FIG. 8 is a front view of one specific configuration of the Parallel Detector Array which detects changes in the amplitude and/or phase of the Optical Scanner beam.

FIG. 8a is a front view of another specific configuration of the Parallel Detector Array which detects changes in the amplitude and/or phase of the Optical Scanner beam.

FIG. 8b is a top view of the optics function of an alternative parallel detection configuration which detects changes in the amplitude and/or phase of the Optical Scanner beam.

FIG. 8c is a front view of another specific configuration of the Parallel Detector Array which detects changes in the amplitude and/or phase of the Optical Scanner beam.

DESCRIPTION OF THE PREFERRED EMBODIMENT

Figure 1:
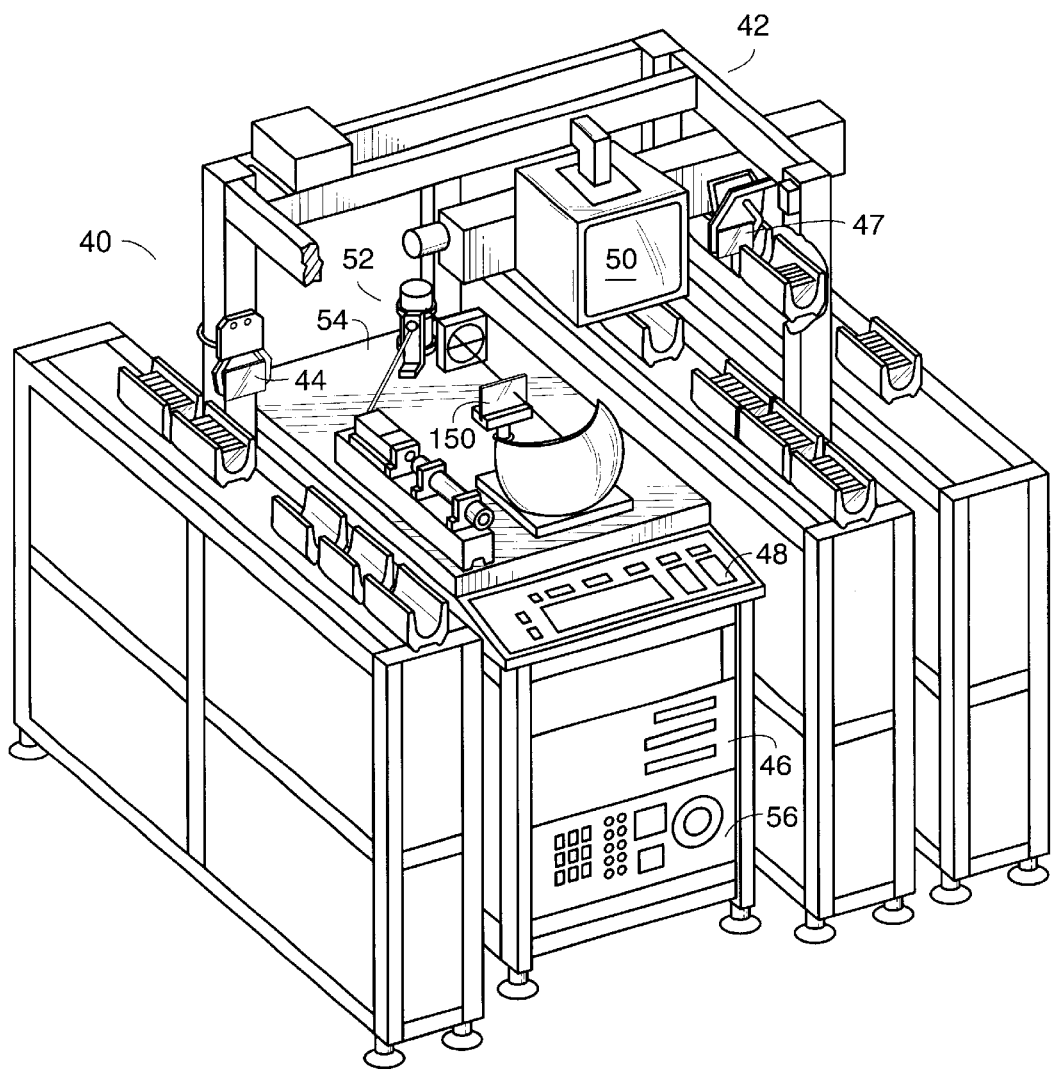
FIG. 1 is a perspective view of the optical inspection apparatus of the present invention.
Figure 2:
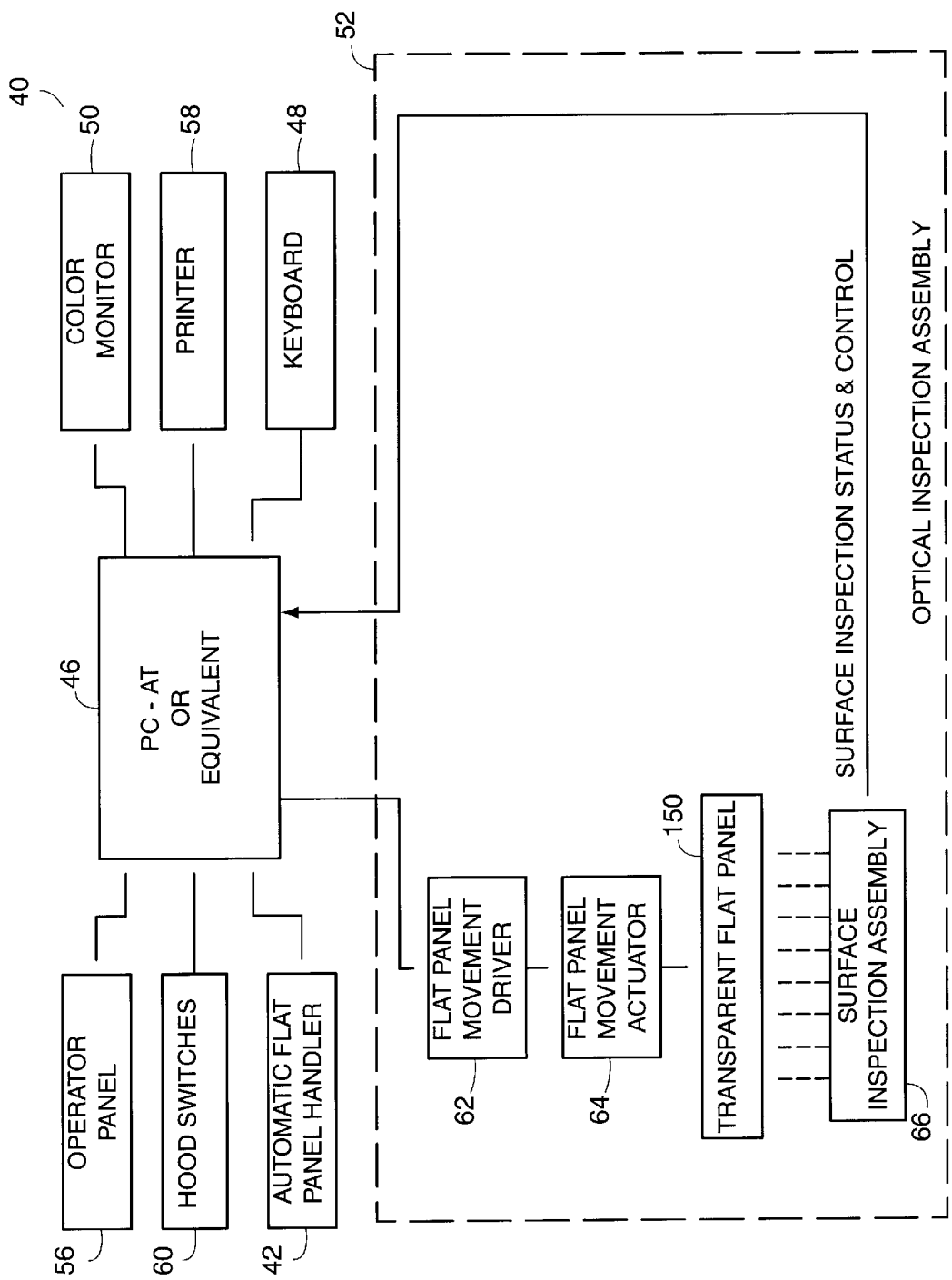
FIG. 2 is a block diagram of the optical inspection apparatus of FIG. 1.

FIG. 1 shows the optical inspection apparatus 40 of the present invention, comprising an IBM compatible PC-AT computer 46 or equivalent, a keyboard 48, a color monitor 50, an operator panel 56, an Optical Inspection Assembly 52 located on table 54, and an Automatic Flat Panel Handler 42 (typically a robot) to automatically load and unload the flat panel to be inspected (44, 150, and 47) into the Optical Inspection Assembly 52. FIG. 2 is the block diagram of the apparatus 40 of the present invention, with numbers that correspond to numbers in FIG. 1 representing the same components. The apparatus shown in FIG. 2 includes a printer 58, and hood switches 60 for detecting when the apparatus 40 is ready for operation. These hood switches 60 act as safety devices, inhibiting operation of the apparatus 40 until the apparatus 40 is in the correct configuration with all hoods secured properly. The Optical Inspection Assembly 52 comprises a Flat Panel Movement Driver 62, a Flat Panel Movement Actuator 64, a Surface Inspection Assembly 66, and a Transparent Flat Panel 150.

The Automatic Flat Panel Handler 42 first loads the Transparent Flat Panel 150 into the Optical Inspection Assembly 52. The Surface Inspection Assembly 66 then begins its scan of the surface of the Transparent Flat Panel 150. The Surface Inspection Assembly 66 performs only a linear inspection, and thus depends on the Flat Panel Movement Actuator 64 to move the Transparent Flat Panel 150 such that the entire surface is inspected by the Surface Inspection Assembly 66.

The Surface Inspection Assembly 66 has a programmable threshold that determines the characteristics of allowable defects. If this assembly detects a defect greater than the programmed threshold, a fault signal is sent to the computer 46 to indicate that the inspection failed. The computer 46 causes the Automatic Flat Panel Handler 42 to place good flat panels (those that pass inspection) in one place, and to place bad flat panels (those that fail inspection) in a different place. In a fully automated system, an automated cart or conveyer would deliver uninspected flat panels and take away both good and bad inspected flat panels as the apparatus 40 requires.

Figure 3:
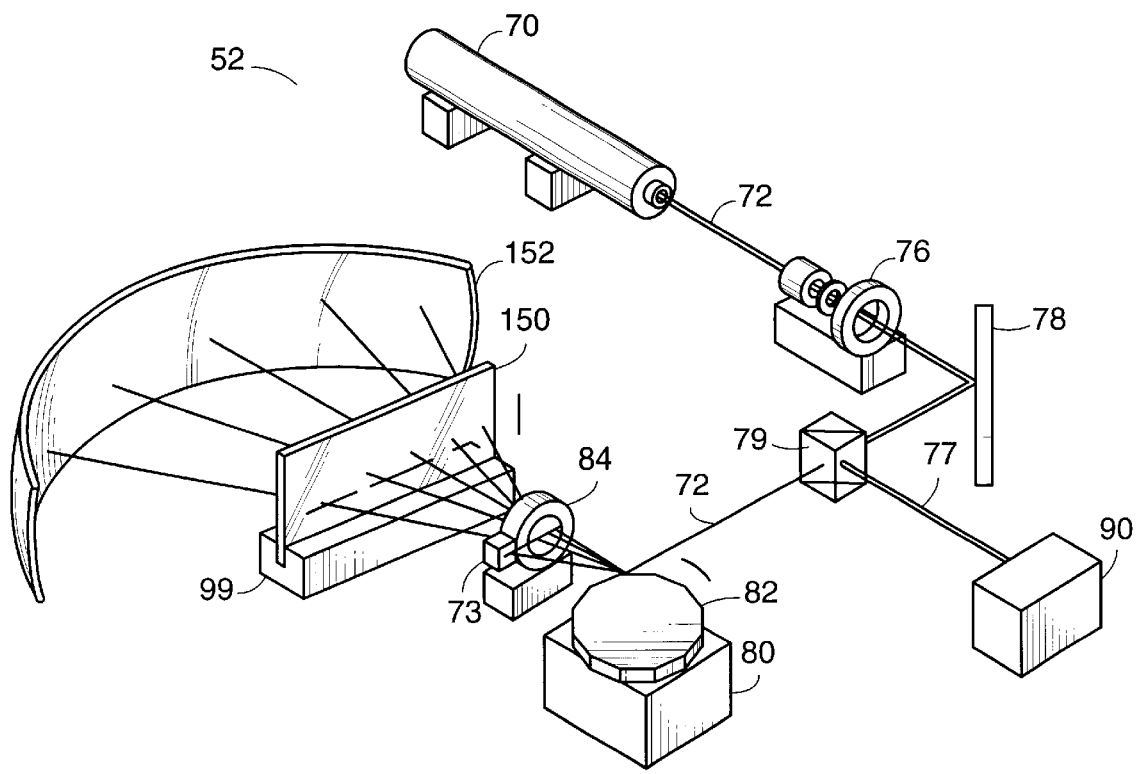
FIG. 3 is a perspective view of the Optical Inspection Assembly used in the apparatus shown in FIG. 1.

The Optical Inspection Assembly 52 for the preferred embodiment of the present invention is shown in FIG. 3. A laser 70 provides the light beam 72 used to inspect the Transparent Flat Panel 150. The laser 70 must have a minimum spatial and temporal coherence greater than the defects to be measured. The coherence of the laser 70 is related to its optical Signal to Noise (S/N) ratio, while the power of the laser 70 is related to its electrical S/N ratio. The light beam 72 passes through Filter Optics 76, which increases the spatial coherence of the beam 72 and shapes and directs the beam 72 to the mirror 78, which directs the beam 72 to Optical Scanner 80. Optical Scanner 80 has a rotating polygonal head 82 with reflective faces. The mirror 78 directs the beam 72 to the rotating polygonal head 82, which causes the beam 72 to sweep across the Scanning Optics 84. If the polygonal head 82 rotates clockwise as shown, the sweep of the beam 72 will be from left to right on the Transparent Flat Panel 150.

Figure 4:
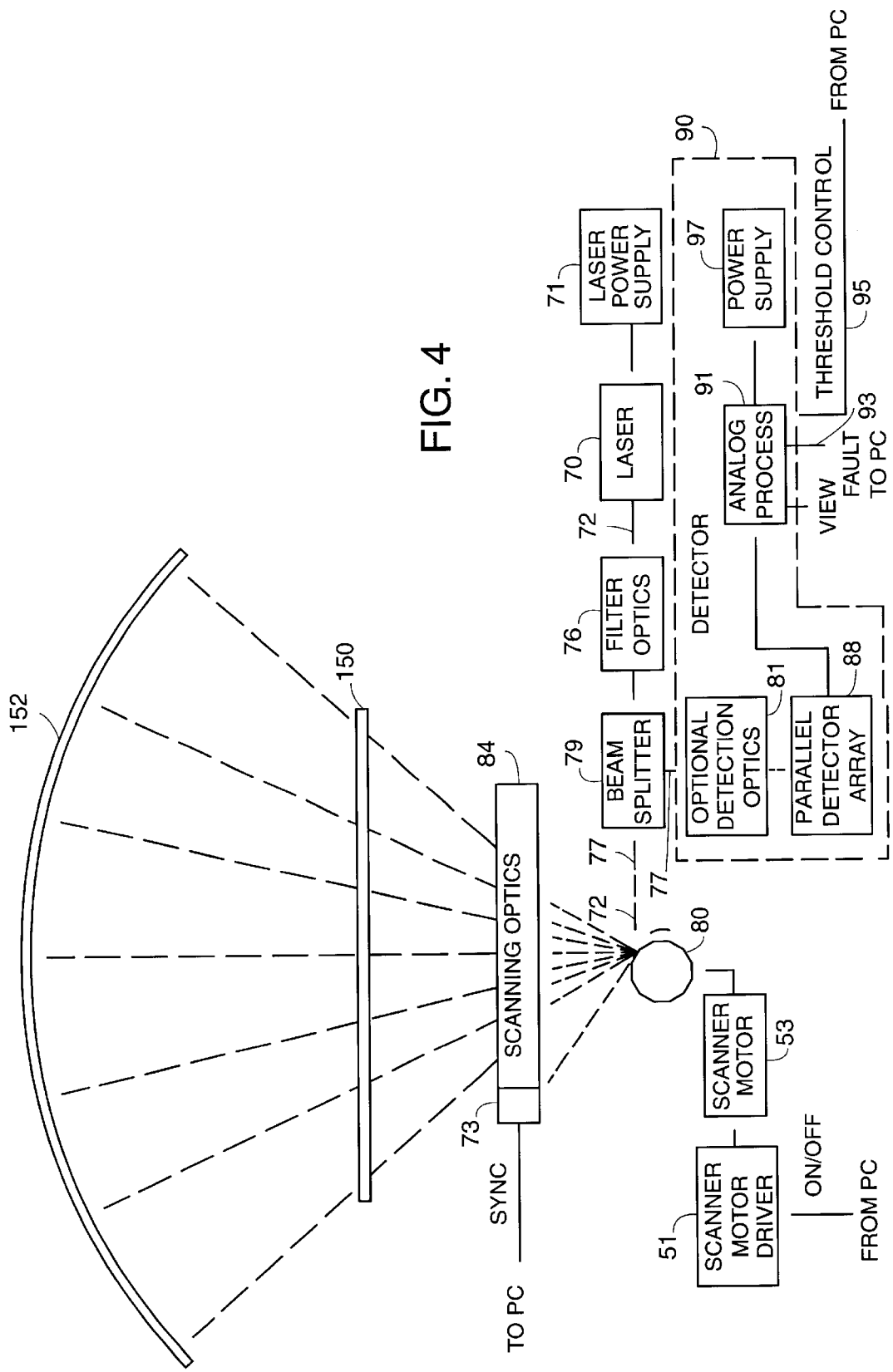
FIG. 4 is a block diagram of the Surface Inspection Assembly within the Optical Inspection Assembly shown in FIGS. 2 and 3.

In the preferred embodiment of the present invention as shown in FIGS. 3 and 4, the Transparent Flat Panel 150 is inspected. In this configuration there is no separate Detection Optics, but the light beam 72 is reflected back to the Scanning Optics 84, which directs the reflected beam 77 (still coincident with the transmitted beam 72) to the Optical Scanner 80, then to a Beam Splitter 79. The Beam Splitter 79 directs the reflected beam 77 to the Parallel Detector Array 88 within Detector 90.

One specific implementation of the Parallel Detector Array 88 is shown in more detail in FIG. 8. An array of light sensitive devices 94 is provided, typically a photodiode array. Each light sensitive device 94 provides an electrical signal proportional to the intensity of light it detects. A nominal beam spot 92 is shown, which is smaller than the matrix as shown. This type of a spot 92 of laser light on Parallel Detector Array 88 causes a two-dimensional response with respect to intensity or amplitude, which is represented in FIG. 7a. Likewise, this type of spot 92 causes a two-dimensional response with respect to changes of phase, which is represented in FIG. 7b. The changes of phase will create an interference pattern between the center and outer rim of the beam 72, causing a change in the ideal Gaussian distribution.

Note that the light sensitive devices 94 of Parallel Detector Array 88 could also be an array of CCDS, and could be arranged in any physical configuration, such as circular or concentric rings of individual detectors, as shown in FIG. 8a. In addition, two concentric ring detectors in the configuration shown in FIG. 8c could be used to form Parallel Detector Array 88. Detector 94a detects the center portion of the beam, while detector 94b detects the outer portion of the beam, which has nominal spot size 92 as shown.

FIG. 8b shows an alternative arrangement which uses two Parallel Detector Arrays 88. Beam 72 has a nominal spot size 92 as shown. Beam 72 is projected onto a transparent substrate 87 which has a small reflective portion 89, and is positioned at a 45 degree angle with respect to the beam 72 as shown. In this manner the center portion 85 of beam 72 is reflected off the reflective portion 89 of transparent substrate 87 to a Parallel Detector Array 88a as shown in the figure. The outer portion 83 of the beam 72 passes through the transparent substrate 87 onto a second Parallel Detector Array 88b. In this manner the two Parallel Detector Arrays 88a and 88b act in parallel to detect any change in the nominal Gaussian distribution of light within beam 72.

Note that the Parallel Detector Arrays 88a and 88b shown in FIG. 8b could be replaced with a single detector, since the two detectors 88a and 88b act in parallel, and can therefore detect with only two sensors changes in the nominal Gaussian distribution of the beam 72. Neither the number, type of device used nor the physical arrangement of these devices is critical to this invention. The primary inventive feature regarding the Parallel Detector Array 88 is the use of more than one optical detector in parallel to detect changes in a nominally Gaussian distribution of light within the spot of the optical beam 72.

By measuring changes in the Gaussian distribution of light, the apparatus 40 of the present invention has a much higher resolution than prior art optical inspection systems, which are limited by the diffraction limits of the optics and specific configuration of the system. By measuring changes in the Gaussian distribution of the beam 72, the apparatus 40 measures changes in the electromagnetic fields in a general point in space, which therefore removes the classical diffraction limit experienced by prior art systems. Since the Parallel Detector Array 88 can detect changes in both phase and amplitude of the nominal Gaussian distribution of light (phase changes are detected by interference between the center and rim of the beam), a change in the surface characteristics caused by even a very narrow or shallow defect will interfere with the rest of the field, and will be detected. This allows the lateral resolution of the apparatus 40 to be from 100 to 1000 times greater than the diffraction limit, since phase changes are detected as well as amplitude changes. In addition, the longitudinal sensitivity within the diffraction limit is interferometric, while the adjustment sensitivity is only dependent on the depth of field. These features provide for a highly sensitive inspection apparatus 40, which can detect any changes of the optical characteristics of the inspected surface on the order of $\frac{1}{100}$ to $\frac{1}{1000}$ of the diffraction limit in all three axes.

Since the Transparent Flat Panel 150 is rectangular rather than circular, the Flat Panel Movement Actuator 64 shown in FIG. 2 is a lifter 99 as shown in FIG. 3. The lifter 99 moves the Transparent Flat Panel 150 during the inspection. For example, during inspection, the lifter 99 positions the Transparent Flat Panel 150 such that the first scan of beam 72 scans the uppermost row of the Transparent Flat Panel 150. As the beam 72 scans the Transparent Flat Panel 150, the lifter 99 gradually raises the Transparent Flat Panel 150 such that all portions of the Transparent Flat Panel are scanned by the beam 72.

FIG. 4 shows the configuration of the Surface Inspection Assembly 66 shown in FIG. 2 used in the Optical Inspection Assembly 52. Note that many of the numbers in FIG. 4 correspond to components shown in FIG. 3. The laser 70 is powered by a Laser Power Supply 71, and provides beam 72, which passes through Filter Optics 76. The mirror 78 of FIG. 3 is not shown in FIG. 4. The light beam 72 contacts the Optical Scanner 80, which provides a linear scanning action of the beam 72 across Trigger Detector 73 and Scanning Optics 84. Trigger Detector 73 is placed at the beginning position of the scan path of beam 72, and provides an electrical SYNC signal to the computer 46 when the beam 72 contacts it to synchronize the sweep of beam 72 with the movement of the Transparent Flat Panel 150 and the output of Detector 90. Note that the Optical Scanner 80 can be switched on or off by the computer 46 giving the appropriate command to the Scanner Motor Driver 51, which controls the Scanner Motor 53. Also note that the Trigger Detector 73 can be mounted anywhere within the scan path of beam 72. In the configuration illustrated in the figures, Trigger Detector 73 is mounted on the side of the Scanning Optics 84. The Trigger Detector 73 could, in the alternative, be placed in the scan path of beam 72 next to the Transparent Flat Panel 150. By placing the Trigger Detector 73 next to the Scanning Optics 84, no optic field of Scanning Optics 84 is taken by Trigger Detector 73.

Figure 5:
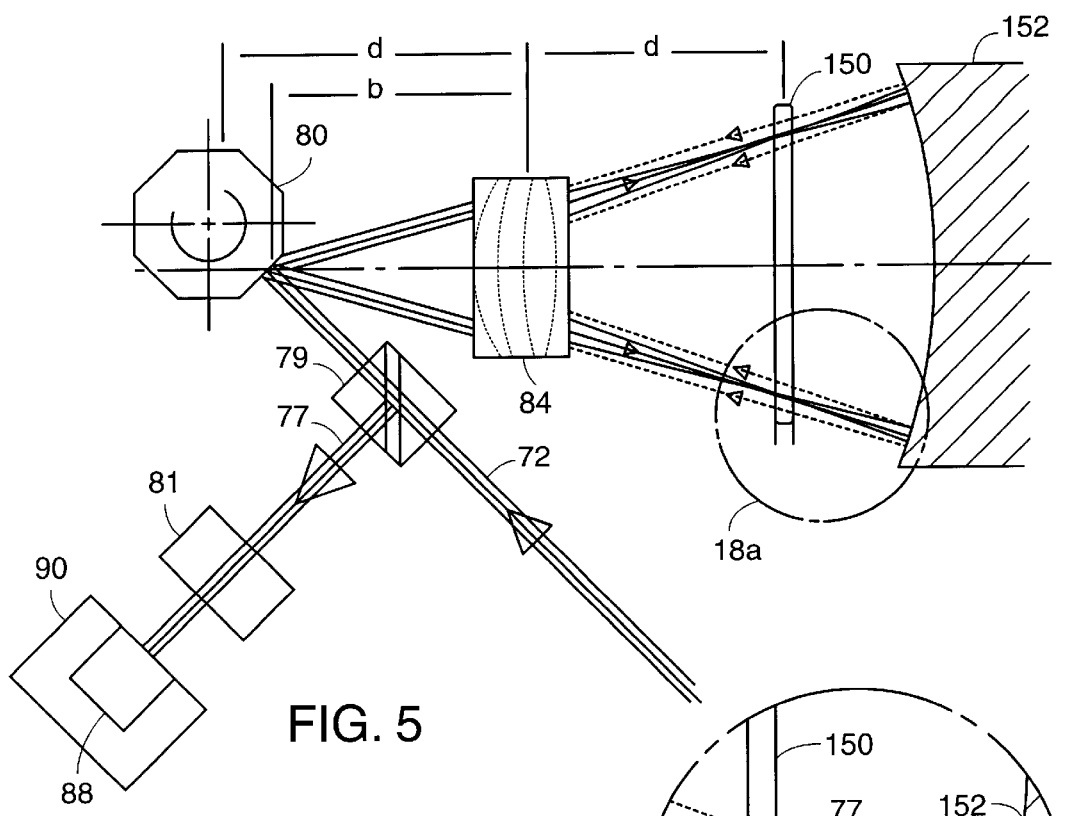
FIG. 5 is a top view of the Optical Scanner and optics function in the Surface Inspection Assembly shown in FIG. 4.
Figure 5A:
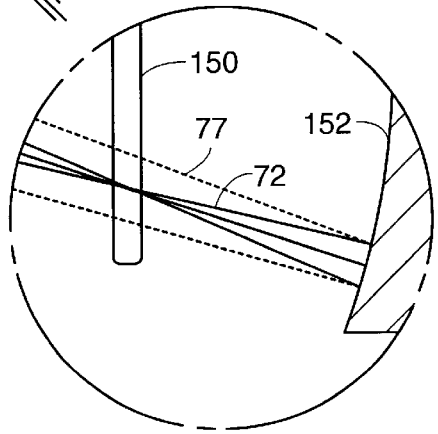
FIG. 5a is an enlarged view of the circular area shown in FIG. 5.

Many typical flat panels are larger than the size of a practical lens. For this reason the Scanning Optics 84 are placed in a position relative to the Optical Scanner 80 which is less than the focal length of Scanning Optics 84. This relationship is shown in FIG. 5 by the distance b from the Optical Scanner 80 to the Scanning Optics 84 being less than the focal length d of Scanning Optics 84. This arrangement causes the beam 72 to diverge at the Scanning Optics 84 as shown in FIG. 5. This feature allows the Scanning Optics 84 to scan a Flat Panel 150 that is larger than the Scanning Optics 84. The beam 72 is focused by Scanning Optics 84 at the exact center of Transparent Flat Panel 150. After the beam 72 passes through Transparent Flat Panel 150, it begins to diverge, and contacts Spherical Mirror 152. The Spherical Mirror 152 reflects beam 72, and this reflected beam 77 is directed back to the Scanning Optics 84. This is shown in more detail in FIG. 5a. Referring again to FIGS. 4 and 5, a Beam Splitter 79 is used to distinguish the reflected beam 77 from the transmitted beam 72, and to direct the reflected beam 77 to the Parallel Detector Array 88 within Detector 90.

The Surface Inspection Assembly 66 in the apparatus 40 of the present invention has its own programmable threshold above which a fault will be signaled, causing the flat panel inspection to fail. In this manner the computer 46 only has to load the flat panel, move the flat panel 150, and monitor the outputs of the Surface Inspection Assembly for faults. If a fault is signaled to the computer 46 prior to the full range of movement of the flat panel 150 being completed, the inspection fails and the flat panel is unloaded by the Automatic Flat Panel Handler 42 and placed in the place for "bad" flat panels. If the computer 46 completes a full movement of the flat panel with no fault signal from the Surface Inspection Assembly, the flat panel passes the inspection and is unloaded by the Automatic Flat Panel Handler 42 and placed in the place for "good" flat panels.

Figure 6:
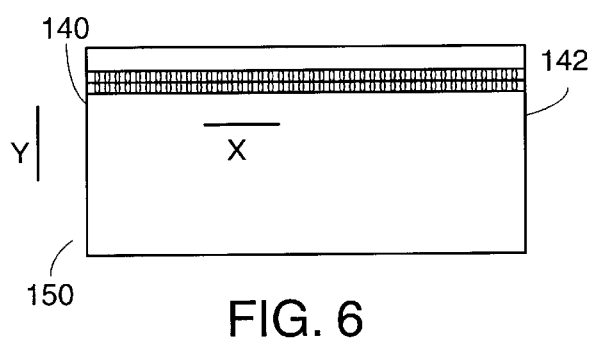
FIG. 6 is a front view of the transparent flat panel shown in FIG. 3 showing the scanning in the x direction, and movement of the flat panel in the y direction.
Figure 6A:
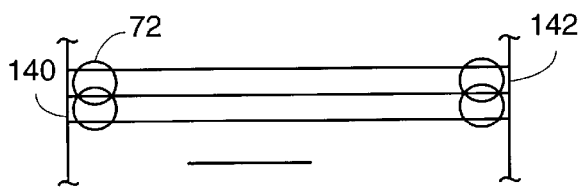
FIG. 6a is an enlarged view of the scanned portion of FIG. 6 showing how the combination of the linear travel of the beam in one direction and the linear movement of the flat panel in a second direction results in complete scanning of the entire surface of the flat panel.

FIG. 6 and 6a illustrate how the combination of the scanning of the beam 72 and the movement of the Transparent Flat Panel 150 provide for a complete inspection of the entire surface of the Transparent Flat Panel 150. As shown in FIG. 6, the beam 72 scans in a line from left to right as shown by the x direction. At the same time the flat panel is moved in the y direction shown in the figure. In this manner the flat panel is inspected in rectangular coordinates, with the x coordinate representing the position of the beam 72 in its scan path, and the y coordinate representing the vertical position of the Transparent Flat Panel 150. The effect of this scanning technique is shown in FIG. 6a.

The beam 72 is configured to scan along the width of the Transparent Flat Panel 150, from left to right as shown. The beam has a spot size which travels along this scan path. In order for the beam 72 to completely scan the entire surface of the Transparent Flat Panel 150, the beam 72 must overlap somewhat with the previous scan path, as shown in the figure. The amount of overlap can be compensated for in software or electronics to provide for accurate mapping of flat panel defects.

Figure 9:
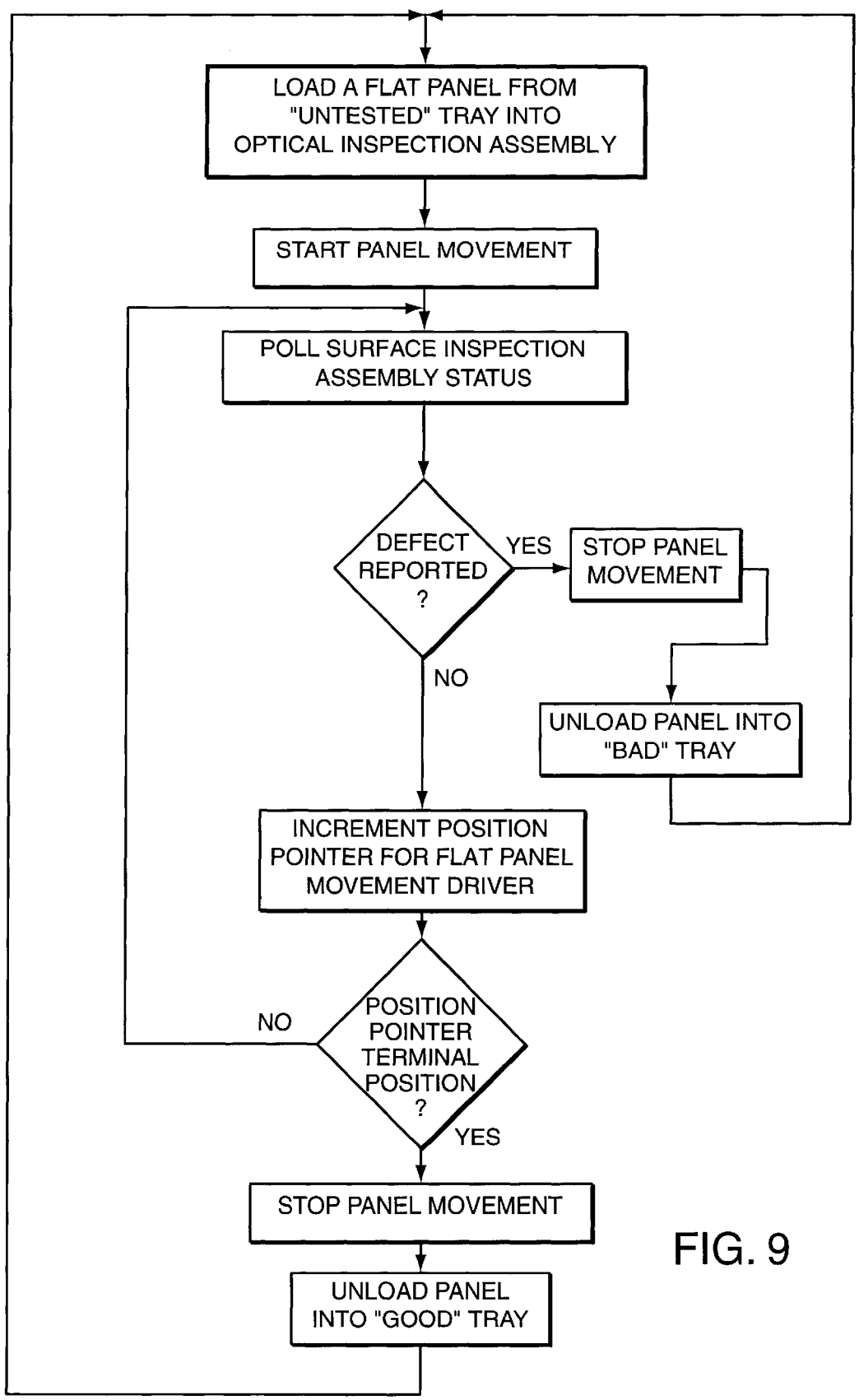
FIG. 9 is a flow chart of the control software operation for the apparatus of the present invention.

The flow chart of the program flow of the control software within computer 46 is shown in FIG. 9. The specific implementation shown in FIG. 9 assumes that the computer 46 will poll the Surface Inspection Assembly 66 to determine whether a defect is reported by this assembly. In an alternative arrangement, the fault output 93 of the Surface Inspection Assembly 66 is an interrupt-driven input to computer 46, which reports a fault by interrupting program execution of the computer 46. In this configuration the computer 46 simply completes the movement of the media, then checks a software flag to determine whether a fault was detected during the scan.

The automation of apparatus 40 provided by computer 46 and Automatic Flat Panel Handler 42 provides for high-speed inspection of apparatus 40, which suits the apparatus 40 well to a speed-sensitive production environment.

While the invention has been described in its preferred embodiments, it is to be understood that the words which have been used are words of description rather than limitation, and that changes may be made within the purview of the appended claims without departing from the true scope and spirit of the invention in its broader aspects.

What is claimed is:

1. An optical inspection apparatus for inspecting a transparent flat panel comprising, in combination:
    computer means for controlling said apparatus;
    operator interface means coupled to said computer means for providing input data from an operator to said computer means and for providing output data from said computer means to said operator;
    an optical inspection assembly, coupled to said computer means having output means for reporting to said computer means results of an inspection performed by said optical inspection assembly, comprising inspection means consisting of detector means for detecting changes of a normal Gaussian distribution of a light beam passing through a transparent flat panel; and
    said transparent flat panel which is placed in said optical inspection assembly to inspect said transparent flat panel for surface defects.

2. The apparatus of claim 1 further comprising automatic media handling means coupled to said computer means for loading under control of said computer means said transparent flat panel into said optical inspection assembly and for unloading under control of said computer means said transparent flat panel out of said optical inspection assembly.

3. The apparatus of claim 1 wherein said computer means comprising, in combination:
    an IBM compatible personal computer; and
    control software means loaded into memory of said IBM compatible personal computer for determining function and sequence of operations of said apparatus.

4. The apparatus of claim 3 wherein said control software comprising:
    a main control program; and
    a plurality of device drivers which provide subroutines for said main control program and which control individual components of said apparatus.

5. The apparatus of claim 1 wherein said computer means periodically polls said output means of said optical inspection assembly to determine whether a surface defect has been detected by said optical inspection assembly.

6. The apparatus of claim 1 wherein said output means of said optical inspection means is coupled to said computer means such that said output means interrupts said computer means when a surface defect is detected by said optical inspection assembly.

7. The apparatus of claim 1 wherein said operator interface means comprising, in combination:
    keyboard means coupled to said computer means for providing said input data from said operator to said computer means; and
    display means coupled to said computer means for displaying said output data from said computer means to said operator.

8. The apparatus of claim 7 wherein said operator interface means further comprising printer means for printing said output data from said computer means.

9. The apparatus of claim 7 wherein said operator interface means further comprising operator panel means having knobs and switches for selecting one of a plurality of detection thresholds for said optical inspection assembly.

10. The apparatus of claim 7 including means for permitting said operator to select one of a plurality of detection thresholds for said optical inspection assembly via said keyboard means.

11. The apparatus of claim 2 wherein said automatic media handling means comprising, in combination:

at least one input tray wherein said transparent flat panel is placed prior to inspection by said apparatus;

at least one movable gripper hand located in proximity to said input tray for gripping and transporting said transparent flat panel from said input tray to said optical inspection assembly;

a first output tray located in proximity to said movable gripper hand such that said transparent flat panel is moved from said optical inspection assembly to said first output tray by said movable gripper hand if said output of said optical inspection assembly signals to said computer means that said transparent flat panel has no surface defects; and a second output tray located in proximity to said movable gripper hand such that said transparent flat panel is moved from said optical inspection assembly to said second output tray by said movable gripper hand if said output of said optical inspection assembly signals to said computer means that said transparent flat panel has surface defects.

12. The apparatus of claim 1 wherein said optical inspection assembly comprising, in combination:

flat panel movement actuator means in physical proximity to said inspection means for moving said transparent flat panel to allow said inspection means to fully inspect said transparent flat panel for surface defects; and flat panel movement driver means electrically coupled to said flat panel movement actuator means and to said computer means for allowing said computer means to control said flat panel movement actuator means by providing appropriate commands to said flat panel movement driver means.

13. The apparatus of claim 12 wherein said flat panel movement actuator means comprising a lifter having a notch wherein an edge of said flat panel is placed and wherein said optical inspection assembly providing a linear sweep of a light beam on a flat surface of said flat panel, said lifter having a range of motion in a direction normal to a plane created by said linear sweep of said light beam, said lifter being coupled to and controlled by said computer means.

14. The apparatus of claim 12 wherein said inspection means is a surface inspection assembly means comprising, in combination:

a light source providing said light beam;

optical scanner means in physical proximity to said light source for permitting said light beam to contact said optical scanner means and for reflecting said light beam thereby providing a linear sweep of said light beam;

scanning optics means having a front face portion and a rear face portion for permitting said linear sweep of said light beam to contact said front face portion of said scanning optics means for causing said light beam that contacts said front face portion to exit said rear face portion and to contact said transparent flat panel;

spherical mirror means for reflecting said light beam after passing through said transparent flat panel back through said transparent flat panel to said scanning optics means in a path. coincident with said light beam being directed to said transparent flat panel;

trigger detector means coupled to said computer means and placed within said linear sweep of said light beam for providing a synchronizing electrical signal to said computer means for indicating a position of said light beam along said linear sweep;

beam splitter means through which said light beam passes for separating said light beam being reflected by said spherical mirror means from said light beam being directed to said transparent flat panel;

said detector means receiving said light beam from said beam splitter means and detecting changes of a nominal Gaussian distribution of said light beam, wherein said changes correspond to and identify defects in said flat surface of said transparent flat panel.

15. The apparatus of claim 14 wherein said light source comprising a laser diode and said light beam comprising a laser beam from said laser diode.

16. The apparatus of claim 14 wherein said light source comprising a helium-neon laser, and said light beam comprising a laser beam from said helium-neon laser.

17. The apparatus of claim 14 wherein said optical scanner means having a motor-driven polygonal head coupled to said computer means and having reflective faces such that said light beam contacts said reflective faces of said polygonal head, and having means for rotating of said polygonal head for causing said light beam reflected off said reflective faces to create said linear sweep of said light beam across said scanning optics means.

18. The apparatus of claim 17 wherein said motor-driven polygonal head is turned on and off by said computer means.

19. The apparatus of claim 14 wherein said optical scanner means being located at a distance from said scanning optics means less than the focal length of said scanning optics means.

20. The apparatus of claim 14 wherein said scanning optics means focus said light beam on said transparent flat panel.

21. The apparatus of claim 14 wherein said trigger detector means comprising an optical sensor having an electrical output corresponding to the presence of said light beam on said optical sensor which is coupled to said computer means.

22. The apparatus of claim 21 wherein said optical sensor comprising a photodiode.

23. The apparatus of claim 21 wherein said optical sensor comprising a charge-coupled device (CCD).

24. The apparatus of claim 14 wherein said detector means comprising, in combination:

at least two optical detectors having electrical outputs, said optical detectors functioning in parallel; and electronic circuitry means for processing said electrical outputs of said optical detectors and generating an electrical signal to said computer means comprising, in combination:

first input means coupled to said electrical outputs of said optical detectors for monitoring said electrical outputs;

second input means coupled to said computer means for receiving a threshold value from said computer means;

processing means coupled to said first input means and to said second input means for measuring said electrical outputs of said optical detectors and for determining the existence of changes of said nominal Gaussian distribution of said light beam above said threshold value on said second input means; and output means coupled to said computer means for signaling an occurrence of a change above said threshold value to said computer means.

25. The apparatus of claim 24 wherein said optical detectors comprise photodiodes.

26. The apparatus of claim 24 wherein said optical detectors comprise charge-coupled devices (CCDs).

27. The apparatus of claim 24 wherein said optical detectors are arranged in rows and columns to form a substantially square matrix.

28. The apparatus of claim 24 wherein said optical detectors are arranged in a series of concentric circular rings.

29. The apparatus of claim 14 further comprising filter optics means for increasing spatial coherence of said light beam.

30. A method for inspecting a transparent flat panel using an optical inspection apparatus including the steps of:
   providing computer means for controlling said apparatus;
   providing operator interface means coupled to said computer means for providing input data from an operator to said computer means and for providing output data from said computer means to said operator;
   providing an optical inspection assembly, coupled to said computer means having output means for reporting to said computer means results of an inspection performed by said optical inspection assembly, comprising inspection means consisting of detector means for detecting changes of a nominal Gaussian distribution of a light beam passing through a transparent flat panel; and
   providing said transparent flat panel which is placed in said optical inspection assembly to inspect said transparent flat panel for surface defects.

31. The method of claim 30 further comprising the step of providing automatic media handling means coupled to said computer means for loading under control of said computer means said transparent flat panel into said optical inspection assembly and for unloading under control of said computer means said transparent flat panel out of said optical inspection assembly.

32. The method of claim 30 wherein said computer means comprising, in combination:
   an IBM compatible personal computer; and
   control software means loaded into memory of said IBM compatible personal computer for determining function and sequence of operations of said apparatus.

33. The method of claim 30 wherein said computer means periodically polls said output means of said optical inspection assembly to determine whether a surface defect has been detected by said optical inspection assembly.

34. The method of claim 30 wherein said output means of said optical inspection means is coupled to said computer means such that said output means interrupts said computer means when a surface defect is detected by said optical inspection assembly.

35. The method of claim 30 wherein said operator interface means comprising, in combination:
   keyboard means coupled to said computer means for providing said input data from said operator to said computer means; and
   display means coupled to said computer means for displaying said output data from said computer means to said operator.

36. The method of claim 35 wherein said operator interface means further comprising operator panel means having knobs and switches for selecting one of a plurality of detection thresholds for said optical inspection assembly.

37. The method of claim 35 including means for permitting said operator to select one of a plurality of detection thresholds for said optical inspection assembly via said keyboard means.

38. The method of claim 31 wherein said automatic media handling means comprising, in combination:
   at least one input tray wherein said transparent flat panel is placed prior to inspection by said apparatus;
   at least one movable gripper hand located in proximity to said input tray for gripping and transporting said transparent flat panel from said input tray to said optical inspection assembly;
   a first output tray located in proximity to said movable gripper hand such that said transparent flat panel is moved from said optical inspection assembly to said first output tray by said movable gripper hand if said output of said optical inspection assembly signals to said computer means that said transparent flat panel has no surface defects; and
   a second output tray located in proximity to said movable gripper hand such that said transparent flat panel is moved from said optical inspection assembly to said second output tray by said movable gripper hand if said output of said optical inspection assembly signals to said computer means that said transparent flat panel has surface defects.

39. The method of claim 30 wherein said optical inspection assembly comprising, in combination:
   flat panel movement actuator means in physical proximity to said inspection means for moving said transparent flat panel to allow said inspection means to fully inspect said transparent flat panel for surface defects; and
   flat panel movement driver means electrically coupled to said flat panel movement actuator means and to said computer means for allowing said computer means to control said flat panel movement actuator means by providing appropriate commands to said flat panel movement driver means.

40. The method of claim 39 wherein said flat panel movement actuator means comprising a lifter having a notch wherein an edge of said flat panel is placed and wherein said optical inspection assembly providing a linear sweep of a light beam on said flat surface of said flat panel, said lifter having a range of motion in a direction normal to a plane created by said linear sweep of said light beam, said lifter being coupled to and controlled by said computer means.

41. The method of claim 39 wherein said inspection means comprises surface inspection assembly means comprising, in combination:
   a light source providing said light beam;
   optical scanner means in physical proximity to said light source for permitting said light beam to contact said optical scanner means and for reflecting said light beam thereby providing a linear sweep of said light beam;
   scanning optics means having a front face portion and a rear face portion for permitting said linear sweep of said light beam to contact said front face portion of said scanning optics means for causing said light beam that contacts said front face portion to exit said rear face portion and to contact said transparent flat panel;
   spherical mirror means for reflecting said light beam after passing through said transparent flat panel back through said transparent flat panel to said scanning optics means in a path coincident with said light beam being directed to said transparent flat panel;
   trigger detector means coupled to said computer means and placed within said linear sweep of said light beam for providing a synchronizing electrical signal to said computer means for indicating a position of said light beam along said linear sweep;
   beam splitter means through which said light beam passes for separating said light beam being reflected by said spherical mirror means from said light beam being directed to said transparent flat panel;

said detector means for receiving said light beam from said beam splitter means and for detecting changes of a nominal Gaussian distribution of said light beam, said changes corresponding to and identifying defects in said flat surface of said transparent flat panel.

42. The method of claim 41 wherein said optical scanner means having a motor-driven polygonal head coupled to said computer means and having reflective faces such that said light beam contacts said reflective faces of said polygonal head, and having means for rotating said polygonal head for causing said light beam reflected off said reflective faces to create said linear sweep of said light beam across said scanning optics means.

43. The method of claim 42 wherein said motor-driven polygonal head is turned on and off by said computer means.

44. The method of claim 41 wherein said optical scanner means being located at a distance from said scanning optics means less than the focal length of said scanning optics means.

45. The apparatus of claim 41 wherein said scanning optics means focus said light beam on said transparent flat panel.

46. The method of claim 41 wherein said trigger detector means comprising an optical sensor having an electrical output corresponding to the presence of said light beam on said optical sensor which is coupled to said computer means.

47. The method of claim 41 wherein said detector means comprising, in combination:
- at least two optical detectors having electrical outputs, said optical detectors functioning in parallel; and
- electronic circuitry means for processing said electrical outputs of said optical detectors and generating an electrical signal to said computer means comprising, in combination:
  - first input means coupled to said electrical outputs of said optical detectors for monitoring said electrical outputs;
  - second input means coupled to said computer means for receiving a threshold value from said computer means;
  - processing means coupled to said first input means and to said second input means for measuring said electrical outputs of said optical detectors and for determining the existence of changes of said nominal Gaussian distribution of said light beam above said threshold value on said second input means; and
  - output means coupled to said computer means for signaling an occurrence of a change above said threshold value to said computer means.

48. The method of claim 47 wherein said optical detectors are arranged in rows and columns to form a substantially square matrix.

49. The method of claim 47 wherein said optical detectors are arranged in a series of concentric circular rings.

50. The method of claim 41 further comprising the steps of:
loading said transparent flat panel into said flat panel movement actuator means in said optical inspection assembly;
activating said surface inspection assembly means with said computer means;
said computer means providing commands to said flat panel movement driver, thereby causing said flat panel movement actuator to move said transparent flat panel such that the entirety of said flat surface is inspected;
checking with said computer means said output of said optical inspection assembly to determine whether a defect was detected by said optical inspection assembly; and
unloading said transparent flat panel from said optical inspection assembly into a first destination if said output on said optical inspection assembly did not indicate the presence of a defect on said transparent flat panel, and unloading said transparent flat panel from said optical inspection assembly into a second destination if said output of said optical inspection assembly did indicate the presence of a defect on said transparent flat panel.

51. An apparatus for optically scanning a transparent flat panel comprising, in combination:
a light source providing a light beam;
light beam reflecting means for reflecting said light beam for providing a linear sweep of said light beam;
a transparent flat panel having a flat surface to be inspected positioned in said linear sweep of said light beam;
detector means for receiving said light beam after it has passed through said transparent flat panel and for detecting changes of a nominal Gaussian distribution of said light beam corresponding to defects in said flat surface of said transparent flat panel; and
means for moving said transparent flat panel within said linear sweep of said light beam and for permitting a linear scan of said flat surface for complete scanning of all of said flat surface to be inspected.

52. The apparatus of claim 51 wherein said light source comprising a laser diode and said light beam comprising a laser beam from said laser diode.

53. The apparatus of claim 51 wherein said light source comprising a helium-neon laser, and said light beam comprising a laser beam from said helium-neon laser.

54. The apparatus of claim 51 wherein said light beam reflecting means comprising an optical scanner.

55. The apparatus of claim 54 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

56. The apparatus of claim 51 wherein said means for moving said transparent flat panel comprising a lifter having a notch wherein an edge of said flat panel is placed, said lifter having a range of motion in a direction normal to a plane created by said linear sweep of said light beam, said lifter being coupled to and controlled by said computer means.

57. A method for optically scanning a transparent flat panel comprising, in combination:
providing a light source having a light beam;
providing light beam reflecting means for reflecting said light beam for providing a linear sweep of said light beam;
providing a transparent flat panel having a flat surface to be inspected positioned in said linear sweep of said light beam;
providing detector means for receiving said light beam after it has passed through said transparent flat panel and for detecting changes of a nominal Gaussian distribution of said light beam corresponding to defects in said flat surface of said transparent flat panel; and providing means for moving said transparent flat panel within said linear sweep of said light beam and for permitting a linear scan of said flat surface for complete scanning of all of said flat surface to be inspected.

58. The method of claim 57 wherein said light beam reflecting means comprising an optical scanner.

59. The method of claim 58 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

60. The method of claim 57 wherein said means for moving said transparent flat panel comprising a lifter having a notch wherein an edge of said flat panel is placed, said lifter having a range of motion in a direction normal to a plane created by said linear sweep of said light beam.

61. The method of claim 57 further comprising detector means for receiving said light beam and for detecting changes of a nominal Gaussian distribution of said light beam corresponding to defects in said flat surface of said transparent flat panel.

62. The method of claim 57 further comprising the steps of:
placing said transparent flat panel into said means for moving said transparent flat panel; and
activating said means for moving said transparent flat panel causing all of said flat surface to pass through said linear sweep of said light beam.

63. An apparatus for detecting surface defects in a transparent flat panel comprising, in combination:
a light source providing a light beam;
light beam reflecting means for reflecting said light beam for providing a linear sweep of said light beam;
a transparent flat panel having a flat surface to be inspected positioned in said linear sweep of said light beam;
means for moving said transparent flat panel within said linear sweep of said light beam and for permitting a linear scan of said flat surface for complete scanning of all of said flat surface to be inspected; and
detector means for measuring changes in said light beam corresponding to defects on said flat surface of said transparent flat panel, wherein said detector means receives said light beam after it has passed through said transparent flat panel and detects changes of a nominal Gaussian distribution of said light beam, said changes corresponding to defects in said flat surface of said transparent flat panel.

64. The apparatus of claim 63 wherein said light source comprising a laser diode and said light beam comprising a laser beam from said laser diode.

65. The apparatus of claim 63 wherein said light source comprising a helium-neon laser, and said light beam comprising a laser beam from said helium-neon laser.

66. The apparatus of claim 63 wherein said light beam reflecting means comprising an optical scanner.

67. The apparatus of claim 66 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

68. The apparatus of claim 63 wherein said means for moving said transparent flat panel comprising a lifter having a notch wherein an edge of said flat panel is placed, said lifter having a range of motion in a direction normal to a plane created by said linear sweep of said light beam.

69. The apparatus of claim 63 wherein said detector means comprising, in combination:
at least two optical detectors having electrical outputs, said optical detectors functioning in parallel; and
electronic circuitry means for processing said electrical outputs of said optical detectors and generating an electrical signal output in response to changes of a nominal Gaussian distribution of said light beam above a selectable threshold value.

70. A method for detecting surface defects in flat media comprising, in combination:
providing a light source having a light beam;
providing light beam reflecting means for reflecting said light beam for providing a linear sweep of said light beam;
providing a transparent flat panel having a flat surface to be inspected positioned in said linear sweep of said light beam;
providing means for moving said transparent flat panel within said linear sweep of said light beam and for permitting a linear scan of said flat surface for complete scanning of all of said flat surface to be inspected; and
providing detector means for measuring changes in said light beam corresponding to defects on said flat surface of said transparent flat panel, wherein said detector means receives said light beam after it has passed through said transparent flat panel and detects changes of a nominal Gaussian distribution of said light beam, said changes corresponding to defects in said flat surface of said unit test.

71. The method of claim 70 wherein said light beam reflecting means comprising an optical scanner.

72. The method of claim 71 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

73. The method of claim 70 wherein said means for moving said transparent flat panel comprising a lifter having a notch wherein an edge of said flat panel is placed, said lifter having a range of motion in a direction normal to a plane created by said linear sweep of said light beam.

74. The method of claim 70 wherein said detector means comprising, in combination:
at least two optical detectors having electrical outputs, said optical detectors functioning in parallel; and
electronic circuitry means for processing said electrical outputs of said optical detectors and generating an electrical signal output in response to changes of a nominal Gaussian distribution of said light beam above a selectable threshold value.

75. The method of claim 70 further comprising the steps of:
placing said transparent flat panel into said means for moving said transparent flat panel;
activating said means for moving said transparent flat panel causing all of said flat surface to pass through said linear sweep of said light beam; and
activating said detector means.

* * * * *